(12) United States Patent
Knobl et al.

(10) Patent No.: US 10,608,701 B2
(45) Date of Patent: Mar. 31, 2020

(54) SPLITTABLE ROTARY JOINT MODULE WITH CONTACTLESS DATA LINK

(71) Applicant: Schleifring GmbH, Fürstenfeldbruck (DE)

(72) Inventors: Horst Knobl, Schongau (DE); Herbert Staffler, Fürstenfeldbruck (DE)

(73) Assignee: Schleifring GmbH, Fürstenfeldbruck (DE)

( * ) Notice: Subject to any disclaimer, the term of this patent is extended or adjusted under 35 U.S.C. 154(b) by 40 days.

(21) Appl. No.: 16/110,918

(22) Filed: Aug. 23, 2018

(65) Prior Publication Data

US 2019/0067777 A1  Feb. 28, 2019

(30) Foreign Application Priority Data

Aug. 29, 2017 (EP) .................... 17188255

(51) Int. Cl.
| | |
|---|---|
| *H04B 5/00* | (2006.01) |
| *H01P 5/04* | (2006.01) |
| *H04B 1/02* | (2006.01) |
| *A61B 6/03* | (2006.01) |

(52) U.S. Cl.
CPC .............. *H04B 5/0012* (2013.01); *H01P 5/04* (2013.01); *H04B 1/02* (2013.01); *A61B 6/035* (2013.01)

(58) Field of Classification Search
CPC . H01P 5/04; H01P 1/122; H01P 1/062; H04B 5/0012; H04B 1/02; H01R 39/08; A61B 6/035
USPC ................. 333/21 R, 137, 256, 257, 261
See application file for complete search history.

(56) References Cited

U.S. PATENT DOCUMENTS

| | | | |
|---|---|---|---|
| 5,600,697 A | 2/1997 | Harrison | |
| 6,956,450 B1 | 10/2005 | Lohr | |
| 8,260,019 B2 * | 9/2012 | Chandra | ............... A61B 6/035 378/19 |
| 2013/0187740 A1 | 7/2013 | Loiselle et al. | |
| 2013/0214614 A1 | 8/2013 | Krumme | |
| 2015/0265225 A1 | 9/2015 | Crawford et al. | |
| 2016/0211822 A1 | 7/2016 | Weithmann et al. | |

* cited by examiner

*Primary Examiner* — Rakesh B Patel
*Assistant Examiner* — Jorge L Salazar, Jr.
(74) *Attorney, Agent, or Firm* — Quarles & Brady LLP; Yakov Sidorin

(57) ABSTRACT

A rotary joint has a body with an even number of body segments. Each body segment holds one transmission line with one RF signal connector at one end and a termination at the opposing end. The body segments are oriented such, that alternatingly in neighboring segments two RF signal connectors or two terminations are next to each other. Two neighboring body segments are connected by a carrier plate. The carrier plate holds an electronic housing where two RF signal connectors are located next to each other, and provides a connection to the RF signal connectors.

5 Claims, 5 Drawing Sheets

SPLITTABLE ROTARY JOINT MODULE WITH CONTACTLESS DATA LINK

CROSS-REFERENCE TO RELATED APPLICATIONS

This application claims priority from pending European Application No. 17188255.8 filed on Aug. 29, 2017 and now published as EP3449833A1, the disclosure of which is incorporated herein by reference.

BACKGROUND

1. Field of the Invention

The invention relates to rotary joints comprising capacitive couplers for non-contacting or contactless signal and data transmission. Such rotary joints may be used in computer tomography scanners, also called CT scanners.

2. Description of Relevant Art

Capacitive rotary joints are used to couple signals and data between parts rotating against each other. For example, in CT scanners, a rotating x-ray tube and an x-ray detector generate high-speed imaging data. The data may be transmitted from the rotating part to the stationary part. Furthermore, control signals for controlling the device and, specifically, the power supply of the x-ray tube may be transmitted from the stationary part to the rotating part and vice versa. Other applications exist where there exists the need to transmit control signals or data between a rotor and a stator—such as in windmills, revolving transfer machines, bottling plants, packaging machines, or placement heads of insertion machines.

A capacitive rotary joint for CT scanners is disclosed in U.S. Pat. No. 5,600,697. A large diameter rotating ring carries a differentially-driven strip line guiding a signal along this circumference of the ring. At the stationary side, there is a capacitive coupler picking up the signal from the near field of the strip line.

A bidirectional capacitive coupler is disclosed in US 2013/0214614 (now granted as U.S. Pat. No. 9,362,047). Here, the channels for the communication from the rotating side to the stationary side and vice versa are interleaved.

A noise-immune capacitive coupler is disclosed in U.S. Pat. No. 6,956,450 B1. Here, the transmission line is not a strip line, but a low pass filter structure, suitable to suppress high frequency noise. The transmission line is terminated at its ends with the characteristic impedance of the line.

All large rotary joints such as the rotary joints used for CT scanners suffer from the problem that they require a large rotating body or carrier for holding the transmission line, which body or carrier must have a circular shape. Handling and transport of such a large body expensive and time consuming.

SUMMARY

The embodiments are providing a rotary joint containing a contactless data link, which includes a plurality of sections. It should be a simple process to assemble the sections to a full body. Moreover, a disassembly of the so-configured body should be possible without damaging the body itself or further components thereon, such as the transmission line, for example.

In an embodiment, the rotary joint body, holding the transmission line of a contactless data link, includes multiple sections. The body may either have a disk shape or a drum shape. Preferably, the sections are arc segments or circularly shaped segments. Preferably, the body is divided into two or four (or any other number that is multiple of 2) segments, resulting in an even number of segments that most preferably have the same size. In a specific embodiment, the case of two segments, preferably each segment covers 180° of an arc, whereas in the related case of four segments, each segment covers 90° of an arc. Preferably, each body segment has a transmission line section, most preferably at the outer side or outer circumference of the segment. Each transmission line section has an RF signal connector at one end and a transmission line termination at the other opposing end. The connector may be a plug connector or a socket connector. The connector may also have any combination thereof or may be hermaphroditic. The transmission line termination terminates the transmission line with the characteristic impedance, such that signals fed through the RF signal connector into the transmission line propagate through the transmission line section and are absorbed in the transmission line termination, preferably without causing any reflections of the signal. Preferably, a transmission line section covers the whole arc section of the body segment. In the case of a 180° body segment, the transmission line section preferably covers an angle of 180°, whereas in the case of a 90° segment, the transmission line section covers an angle of 90°.

For interconnecting the body segments to assemble a full body, preferably mechanical connecting plates are provided. So-structured mechanical connecting plates may be attached to neighboring body segments, for example by means of screws, holding them together. In addition, at least one carrier plate is provided and configured to additionally hold neighboring body segments together. This carrier plate preferably is affixed by screws to neighboring body segments. Furthermore, the carrier plate may carry an electronic housing, which in turn may further include at least one driver configured to generate and/or amplify signals to be fed into the transmission line sections.

Body segments may include a plurality of sub-segments affixed together.

Body segments or sub-segments may be glued, screwed, welded or soldered together.

Neighbored body segment sections are aligned such that the RF signal connectors of neighboring body segments are close together (in close proximity with one another) such that the connectors of an electronic housing may connect two transmission line sections of neighboring body segments at the same time. The use of this kind of connection allows one to avoid mismatch in signal delays and other signal properties such as amplitude or common mode rejection, which may be caused under the circumstances when the same signals are processed by separate driver circuits that are distant from each other, such that different electronic housings are required for such driver circuits. At the end of the body segments that is opposite to the location of an electronic housing, there are only terminations which do not normally require any active electronic, and therefore do not require electronic housing. At these locations, a carrier plate without electronic housing may be provided for firmly holding the body segments together.

BRIEF DESCRIPTION OF THE DRAWINGS

In the following, the invention will be described by way of example(s) of embodiment(s), without limitation of the general inventive concept, and with reference to the drawings.

Figure 1:
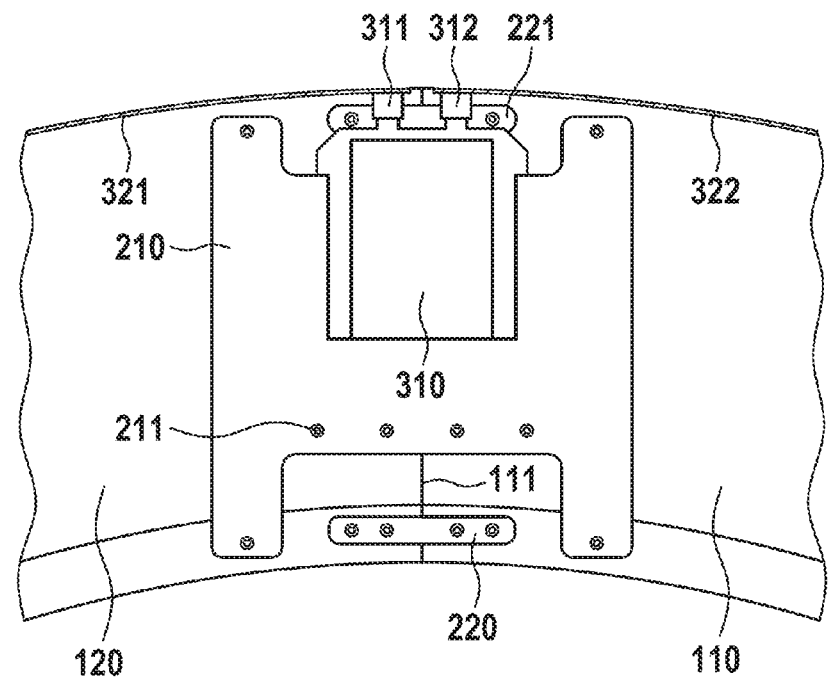
FIG. 1 shows a body segment interconnection.

While various modifications and alternative forms of implementation of the idea of the invention are within the scope of the invention, specific embodiments thereof are shown by way of example in the drawings and are described below in detail. It should be understood, however, that the drawings and related detailed description are not intended to limit the implementation of the invention to any particular form disclosed in this application, but to the contrary, the intention is to cover all modifications, equivalents and alternatives falling within the spirit and scope of the present invention as defined by the appended claims.

DETAILED DESCRIPTION

In FIG. 1, a partial view of a preferred embodiment is shown.

Figure 3:
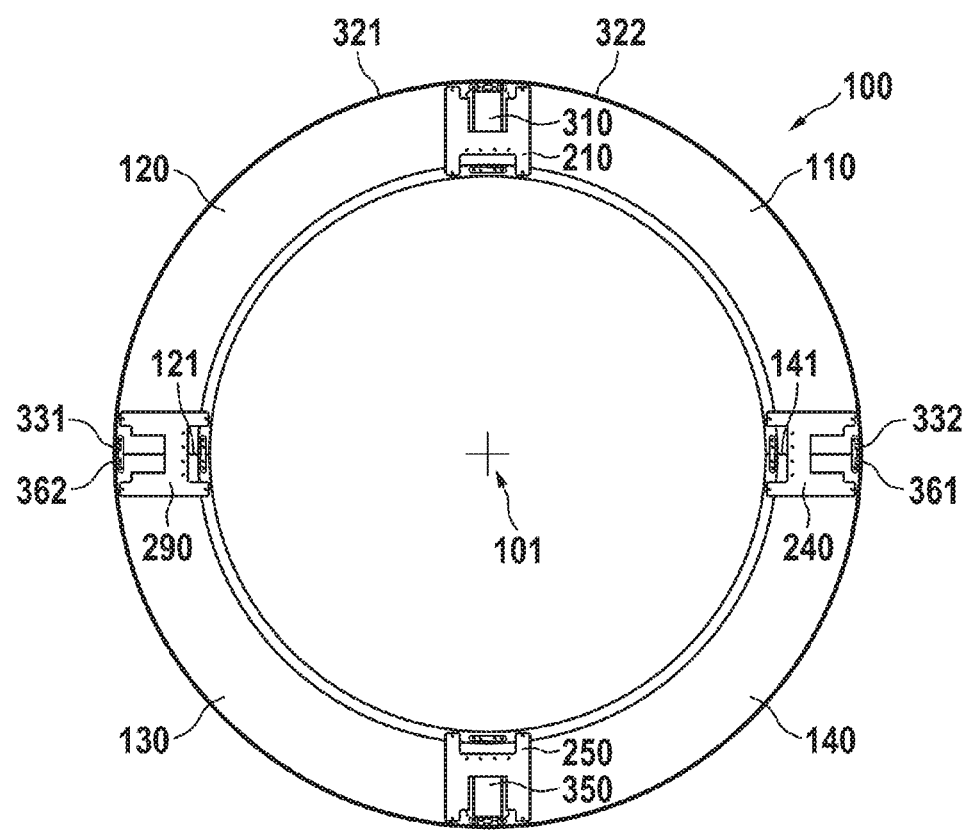
FIG. 3 shows an embodiment of a complete slipring body.

FIG. 1 shows a partial view of the embodiment 100 further illustrated in FIG. 3—specifically, an upper portion located at the intersection or seam 111 between two neighbored body segments 110 and 120 The two neighbored body segments 110, 120 are mechanically held together by at least one connecting plate 220, 221. In one implementation, It is preferred to have at least an inner connecting plate 220 at the inner side of the body (on the side of the inner diameter of the body embodiment 100, as observed in FIG. 3) and an outer connecting plate 221 close to the outer side of the body (on the side of the outer diameter of the body embodiment 100). The connecting plates preferably are affixed by screws 211 to the body segments 110, 120.

Furthermore, a carrier plate 210 is configured to firmly hold the body segments 110 and 120 together. The carrier plate 210 preferably is held by screws 211 to the body segments. An electronic housing 310 is held by the carrier plate 210 at a predetermined position relative to the body segments 110, 120. The electronic housing 310 preferably contains electronic devices such as drivers configured to generate and/or amplify transmission signals that are fed into transmission line sections 321, 322. Preferably, there are multiple transmission line sections at the outer circumference of the body 100. Most preferably, the number of the transmission line sections is a multiple of 2. In the simplest embodiment, there are only two transmission line sections. In a more complex embodiment, there are four transmission line sections, as will be shown later. As is recognized in the prior art, the signals to be coupled via the rotary joint are fed at one end into each transmission line section 321, 322 and propagate through the transmission line section, until they reach a termination 331, 332 at the end of the transmission line section.

The electronic housing and, in particular, the driver circuit contained therein is connected via RF signal connectors 311, 312 to the transmission line sections. As shown in FIG. 1, the first transmission line section 321 is located on the second body segment 120, whereas the second transmission line section 322 is located on the first body segment 110. The first RF signal connector 311, configured to connect the first transmission line section 321, is disposed on the second body segment 120. The second RF signal connector 312, configured to connect the second transmission line section 322, is disposed on first body segment 110.

Preferably, each body segment has its own, respective transmission line section together with its own respective RF signal connector. Such configuration facilitates, for example, easy disassembly. For disassembly of the embodiment shown in FIG. 1, the attachment screws 211 of the carrier plate 210 may to be removed first. Then, the electronic housing 310, which may still be connected to the carrier plate 210, may be unplugged from the RF signal connectors 311, 312. Now, the transmission line sections 321 and 322 are separated from each other, and the body segments 110, 120 are only held together by connecting plates 220, 221, which may be removed later.

The assembly of this embodiment 100 may also be carried out simply by first holding body segments 110 and 120 together with the connecting plates 220, 221, which may be screwed into the body segments. In a next step, the electronic housing 310 together with the attached carrier plate 210 is plugged into the RF signal connectors 311, 312 of transmission line sections 321, 322. Finally, carrier plate 210 is secured to the body segments 110, 120, firmly affixing the body segments together. The intersection or seam 111 is characterized by or associated with the two RF connectors facing each other.

Figure 2:
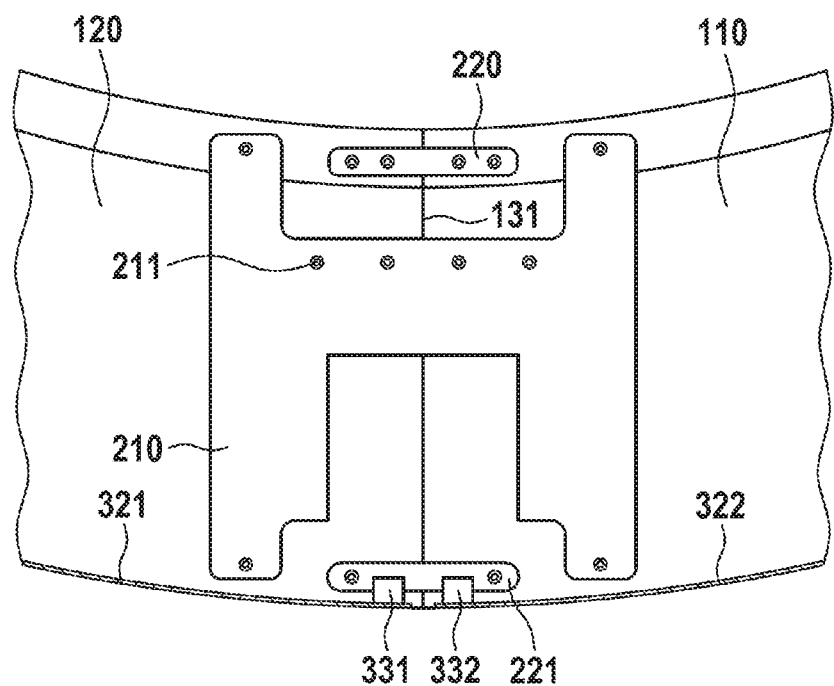
FIG. 2 shows another body segment interconnection.
Figure 5:
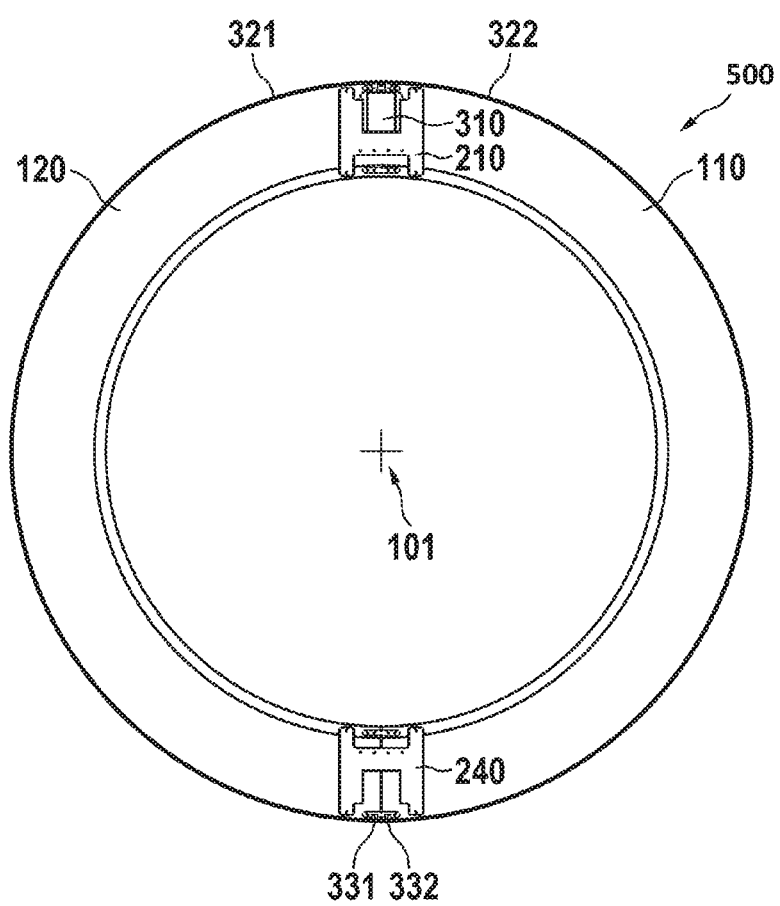
FIG. 5 shows a simplified embodiment.

FIG. 2 shows a carrier plate 210 without electronic housing 310 (corresponding to the lower portion of the embodiment 500, shown in FIG. 5). Such version of the carrier plate, devoid of electronic housing, may be used in the alternative to the carrier plate cooperated with an electronic housing. Carrier plates without electronic housing may be used to hold body segments together, where transmission line terminations 331, 332 are located. Here, connecting plates 220, 221 may be used as well. The intersection or seam formed in FIG. 2 by the segments 110, 120 is characterized by or associated with the two transmission line terminations facing each other.

FIG. 3 illustrates a complete embodiment 100 of the body of the rotary joint, with the rotation axis indicated as 101. This example of the embodiment includes four body segments 110, 120, 130, 140 forming intersections 111, 121, 131, 141. There is a first electronic housing 310 with first carrier plate 210 and opposing thereto a second electronic housing 350 with second carrier plate 250. The first electronic housing 310 with first carrier plate 210 is on the top (an upper portion of the embodiment 100, as seen in FIG. 3) and is connecting body segments 110, 120. The second electronic housing 350 with second carrier plate 250 is at the bottom (the lower portion of the embodiment 100, as seen in FIG. 3), connecting body segments 130, 140. Between the carrier plates with electronic housing, at the locations of terminations 331, 332 there are carrier plates configured to terminate the transmission line, which plates hold or carry no electronic housing. There is a first carrier plate 240 configured to terminate the transmission lines and a second carrier plate 290 configured to terminate the transmission lines opposing thereto. Furthermore, inner connecting plates 220, 221 may be attached at these locations as described in FIG. 1.

The already-assembled body 100 can easily be disassembled into four sections 110, 120, 130, 140, or the body 100 may easily be assembled from four sections 110, 120, 130, 140. These four sections, when separated from one another, require far less space than the whole assembled body. Therefore, the sections can be manufactured easier than the whole integral body and are further saving transport and handling costs.

Here, only electronic housings 310 are required at the top and bottom positions of the body 100 (as seen in FIG. 3;

pairs of RF connectors facing each other at the top and bottom intersections are not shown for simplicity of illustration). At the left and right positions, however, where the terminations are located, electronic housings are not required. Here, carrier plates 240, 290 (without electronic housings) may still be provided to hold the neighboring body segments (110, 140) and (120, 130) together, if the connecting plates are not sufficient by themselves. Accordingly, as seen in FIG. 3, the upper and lower intersections or seams formed by the corresponding neighboring body segments is characterized by or associated with the two RF connectors facing each other, while the intersections or seams on the left- and right-hand sides of the embodiment 100 are characterized by or associated with the two transmission line terminations facing each other. Accordingly, intersections formed by the body segments carry or contain, in an alternative fashion, two RF connectors facing each other and two terminations facing each other.

Figure 4:
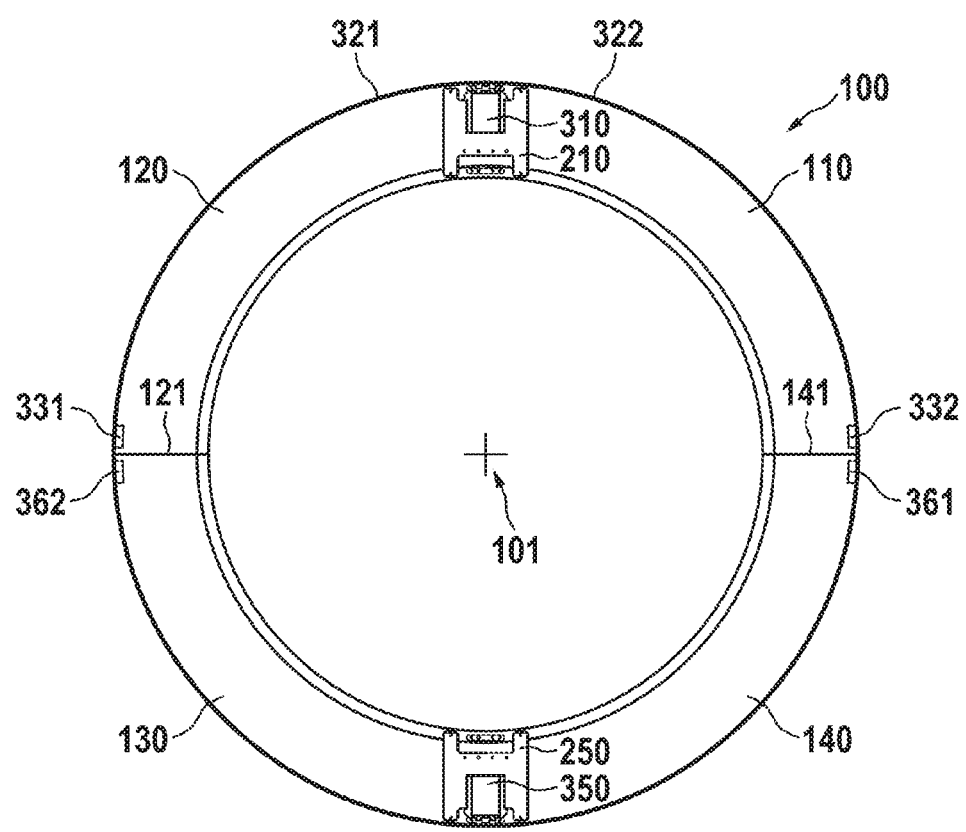
FIG. 4 shows a partial assembled slipring body.

FIG. 4 shows the embodiment of FIG. 3 being partially assembled, without first and second carrier plate 240, 290 configured to terminate transmission line(s). Here, the terminations for the transmission line sections can be seen. For example, the first transmission line section 321 is terminated by the first transmission line termination 331, and the second transmission line section 322 is terminated by the second transmission line termination 332. The third transmission line termination 361 and the fourth transmission line termination 362 are provided for the transmission lines at the body segments 130, 140. These transmission lines are not shown in detail.

FIG. 5 shows a simplified embodiment 500. While similar to the embodiment of FIG. 3, but the body of the embodiment of FIG. 5 has only two body segments. Accordingly, only the first carrier plate 210 with the first electronic housing 310 and a first carrier plate 240 configured to terminate transmission line(s) are required. From the description of various embodiments it is appreciated that body segments are preferably compiled into the body while being oriented such at each of the intersections or seams formed by the neighboring body segments either two RF signal connectors are facing each other or two terminations of transmission line(s) are facing each other, and such pairs of two RF connectors or two terminations alternate when viewed around the perimeter of the body. For example, if a given intersection formed by the two neighboring segments (from an even number of intersections present in the embodiment) is associated with or contains two RF connectors (one belonging to the first of the two neighboring segment, and another—to the neighboring segments), then the very next intersection of the body is associated with or includes two terminations.

Figure 6:
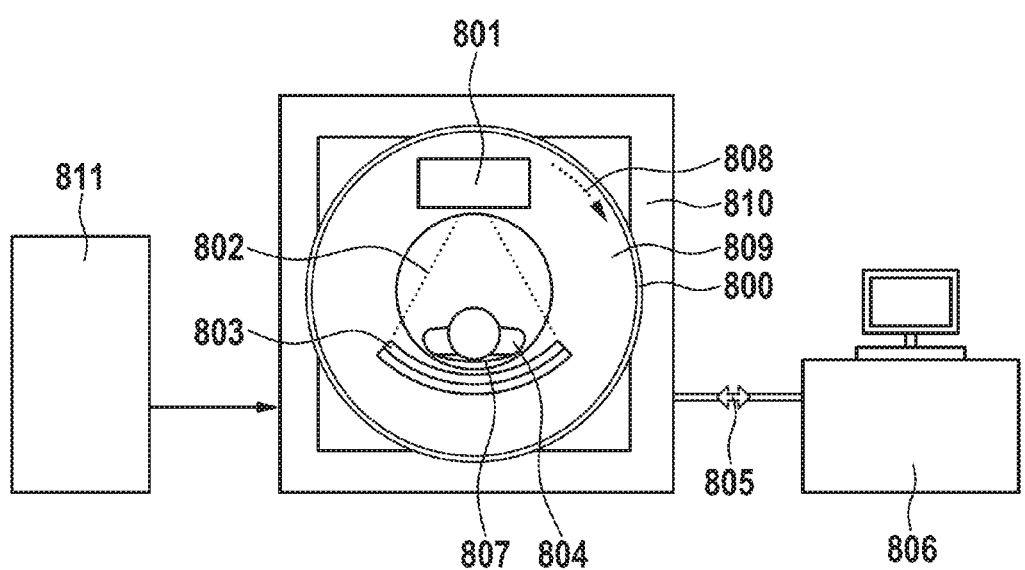
FIG. 6 shows schematically a CT (Computed Tomography) scanner gantry.

FIG. 6 shows schematically a CT (Computed Tomography) scanner gantry. The stationary part is suspended within a massive frame 810. The rotating part 809 of the gantry is rotatably mounted with respect to the stationary part and rotates in the rotation direction 808. It supports an X-ray tube 801 configured to generate an X-ray beam 802 that radiates through a patient 804 lying on a table 807 and which is intercepted by a detector 803 and converted to electrical signals and imaging data thereof. Electrical power from the power supply unit 811 may be transmitted by a slipring (not shown) to the rotating part. The data obtained by the detector 803 are transmitted via contactless rotary joint 800 to an evaluation unit 806 by means of a data bus or network 805.

It will be appreciated to those skilled in the art having the benefit of this disclosure that this invention is believed to provide rotary joints. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

100 body
101 rotation axis
110, 120, 130, 140 body segments
111, 121, 131, 141 segment intersections or seams
210 first carrier plate with housing
211 screws
220 inner connecting plate
221 outer connecting plate
240 first carrier plate for termination (of transmission line(s))
250 second carrier plate with housing
290 second carrier plate for termination
310 first electronic housing
311 first RF signal connectors
312 second RF signal connector
321 first transmission line section
322 second transmission line section
331 first transmission line termination
332 second transmission line termination
350 second electronic housing
361 third transmission line termination
362 fourth transmission line termination
800 contactless rotary joint
801 x-ray tube
802 x-ray beam
803 x-ray detector
804 patient
805 network
806 evaluation unit
807 patient table
808 rotation direction
809 rotating part
810 frame
811 power supply unit

The invention claimed is:

1. A rotary joint comprising:
a body and at least one transmission line for a contactless data link, said at least one transmission line including multiple transmission line sections,
the body including a plurality of body segments,
each body segment of the plurality of body segments including one corresponding transmission line section, said corresponding transmission line section having first and second ends and including one RF signal connector at the first end and a termination at the second end opposing the first end,
the body segments in the body are positioned to form intersections with one another and oriented such that first and second intersections alternate as seen around a perimeter of the body, the first intersection characterized by having two RF signal connectors disposed next to each other respectively at those body segments of the plurality that form said first intersection, the second intersection characterized by having two terminations disposed next to each other respectively at those body segments of the plurality that form said second intersection, two neighboring body segments from said plurality are connected by at least one carrier plate, wherein the at least one carrier plate holds an electronic housing including a connection to the two RF signal connectors.

2. The rotary joint according to claim 1, wherein the body includes an even number of the body segments from the plurality.

3. The rotary joint according to claim 1, wherein the body includes 2 body segments or 8 body segments from the plurality.

4. The rotary joint according to claim 1, wherein the at least one carrier plate is affixed by screws to the two neighboring body segments.

5. The rotary joint according to claim 1, wherein further comprising at least one of an inner connecting plate configured to connect the two neighboring body segments along outer perimeters thereof and an outer connecting plate configured to connect the two neighboring body segments along inner perimeters thereof.

* * * * *